(12) United States Patent
Khera et al.

(10) Patent No.: US 9,351,957 B2
(45) Date of Patent: May 31, 2016

(54) AMORPHOUS FORM OF APREMILAST

(71) Applicant: CADILA HEALTHCARE LIMITED, Ahmedabad, Gujarat (IN)

(72) Inventors: Brij Khera, Gujarat (IN); Kumar Kamlesh Singh, Gujarat (IN); Santosh Devidas Diwakar, Gujarat (IN); Chetan Jayantibhai Vasava, Gujarat (IN); Anil Kumar Shivprasad Tiwari, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 14/677,110

(22) Filed: Apr. 2, 2015

(65) Prior Publication Data

US 2015/0283249 A1    Oct. 8, 2015

(30) Foreign Application Priority Data

Apr. 4, 2014    (IN) .......................... 1283/MUM/2014

(51) Int. Cl.
| | |
|---|---|
| C07D 209/48 | (2006.01) |
| A61K 31/4035 | (2006.01) |
| A61K 9/14 | (2006.01) |
| A61K 9/16 | (2006.01) |

(52) U.S. Cl.
CPC ............... *A61K 31/4035* (2013.01); *A61K 9/14* (2013.01); *A61K 9/146* (2013.01); *A61K 9/1652* (2013.01); *C07D 209/48* (2013.01)

(58) Field of Classification Search
CPC ...................................................... C07D 209/48
See application file for complete search history.

(56) References Cited

U.S. PATENT DOCUMENTS

| | | |
|---|---|---|
| 6,020,358 A | 2/2000 | Muller et al. |
| 7,427,638 B2 | 9/2008 | Muller et al. |
| 7,893,101 B2 | 2/2011 | Muller et al. |
| 2013/0217918 A1 | 8/2013 | Venkateswaralu et al. |
| 2014/0081032 A1 | 3/2014 | Connoly et al. |

FOREIGN PATENT DOCUMENTS

| | | |
|---|---|---|
| WO | WO 2009/120167 | 10/2009 |
| WO | WO 2012/097116 | 7/2012 |
| WO | WO 2014/072259 | 5/2014 |

*Primary Examiner* — Shawquia Jackson
(74) *Attorney, Agent, or Firm* — Ladas & Parry LLP

(57) ABSTRACT

The present invention provides an amorphous form of apremilast and process for preparation thereof. The present invention also provides a pharmaceutical composition comprising an amorphous apremilast and one or more of pharmaceutically acceptable carriers, excipients or diluents used for the treatment of active psoriatic arthritis.

20 Claims, 3 Drawing Sheets

AMORPHOUS FORM OF APREMILAST

CROSS REFERENCE TO RELATED APPLICATIONS

Figure 1:
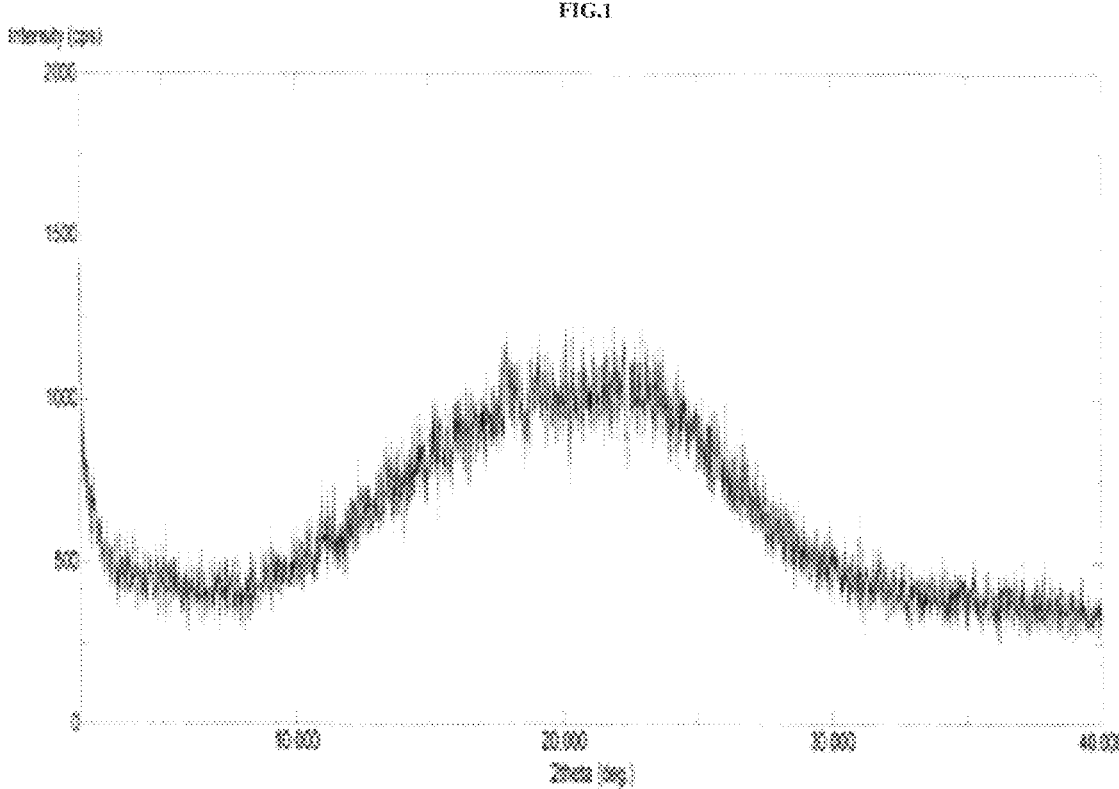

This application claims benefit of Foreign Application INDIA 1283/MUM/2014 filed on Apr. 4, 2014.

FIELD OF THE INVENTION

The present invention relates to an amorphous form of apremilast. In particular, the present invention relates to processes for the preparation of amorphous form of apremilast. More particular the present invention relates to the pharmaceutical composition comprising an amorphous apremilast and one or more of pharmaceutically acceptable carriers, excipients or diluents used for the treatment of active psoriatic arthritis.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Apremilast is a phosphodiesterase 4 (PDE4) inhibitor. Apremilast is chemically known as N-[2-[(1S)-1-(3-ethoxy-4-methoxyphenyl)-2-(methylsulfonyl)ethyl]-2,3-dihydro-1,3-dioxo-1H-isoindol-4-yl]acetamide having Formula (I).

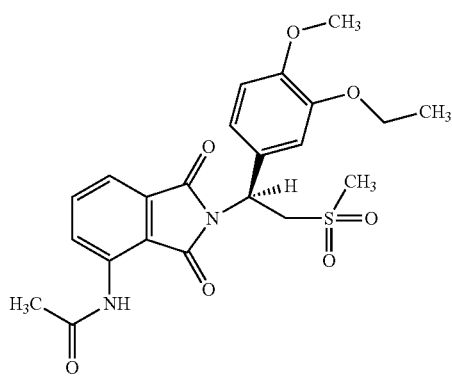

(I)

Apremilast is indicated for the treatment of adult patients with active psoriatic arthritis. It is available under the trade name of OTEZLA® as an inhibitor of phosphodieasterase 4 (PDE4) and OTEZLA tablets are supplied in 10, 20, and 30 mg strengths for oral administration.

U.S. Pat. No. 6,020,358 discloses racemic 2-[1-(3-ethoxy-4-methoxy phenyl)-2-(methylsulfonyl)ethyl]-2,3-dihydro-1,3-dioxo-1H-isoindol-4-yl]acetamide and process for its preparation, which is incorporated herein by reference.

U.S. Pat. No. 7,427,638 discloses stereomerically pure (+)-2-[1-(3-ethoxy-4-methoxyphenyl)-2-methylsulfonylethyl]-4-acetylaminoisoindoline-1,3-dione, substantially free of its (−) isomer, or a pharmaceutically acceptable metabolite, salt, solvate or hydrate, thereof and its pharmaceutical composition. The stereomerically pure (+)-2-[1-(3-ethoxy-4-methoxyphenyl)-2-methylsulfonyl-ethyl]-4-acetylaminoisoindoline-1,3-dione is the (+)-isomer of racemic 2-[1-(3-ethoxy-4-methoxyphenyl)-2-(methylsulfonyl)ethyl]-2,3-dihydro-1,3-dioxo-1H-isoindol-4-yl]acetamide.

WO 2012/097116 and U.S. 2014/0081032 disclose processes for the preparation of isoindoline compounds and their isotopologues including apremilast.

U.S. 2013/0217918 discloses processes for enantioselective preparation of arylmethanesulfonylethylamines using chiral auxiliaries (S)-1-(3-ethoxy-4-methoxyphenyl)-2-methanesulfonylethylamine which is used for the preparation of apremilast.

WO 2009/120167 and U.S. Pat. No. 7,893,101 disclose various solid forms comprising apremilast include single-component and multiple-component forms, including crystal forms and amorphous forms and their mixture comprising one or more of the Forms A, B, C, D, E, F, G and an amorphous solid form and provides representative XRPD patterns, DSC plots, TGA plots and DVS plots for each of Forms A, B, C, D, E, F and G.

WO 2014/072259 discloses pharmaceutical composition of amorphous apremilast with at least one excipients prepared by melt extrusion technique.

There is no disclosure found about the process for the preparation of an amorphous form of apremilast and its characterization as well as physiochemical properties and its stability.

The different physical properties exhibited by polymorphs affect important pharmaceutical parameters such as storage, stability, compressibility, density and dissolution rates (important in determining bioavailability). Stability differences may result from changes in chemical reactivity (e.g., differential hydrolysis or oxidation, such that a dosage form discolors more rapidly when comprised of one polymorph than when comprised of another polymorph), mechanical changes (e.g., tablets crumble on storage as a kinetically favored crystalline form converts to thermodynamically more stable crystalline form) or both (e.g., tablets of one polymorph are more susceptible to breakdown at high humidity).

An amorphous form generally provides better solubility and bioavailability than the crystalline form and may be useful for formulations which can have better stability, solubility and compressibility etc which are important for formulation and product manufacturing.

Therefore, it is desirable to have a stable amorphous form of drug with high purity to meet the needs of regulatory agencies and highly reproducible processes for its preparation.

In view of the above, it is therefore, desirable to provide an efficient, more economical, less hazardous and eco-friendly process for the preparation of amorphous form of apremilast. The amorphous form provided herein is stable under ordinary stability conditions with respect to purity and storage.

SUMMARY OF THE INVENTION

In one general aspect, there is provided an amorphous form of apremilast.

In another general aspect, there is provided an amorphous form of apremilast wherein the amorphous apremilast is free from residual solvents.

In another general aspect, there is provided a process for the preparation of an amorphous form of apremilast, wherein the amorphous form is prepared by milling apremilast for sufficient time.

In another general aspect, there is provided an amorphous solid dispersion of apremilast and a polymer.

In another general aspect, there is provided an amorphous solid dispersion of apremilast wherein the amorphous solid dispersion of apremilast is prepared by a process comprising grinding a solid-solid mixture of apremilast and a polymer.

In another general aspect, there is provided a process for preparing an amorphous solid dispersion of apremilast, wherein the step of grinding a solid-solid mixture of apremilast and a polymer comprises grinding a solid-solid mixture of crystalline apremilast and a polymer.

In another general aspect, there is provided a process for the preparation of an amorphous form of apremilast, the process comprising:
(a) providing a solution of apremilast in one or more of solvents; and
(b) obtaining an amorphous form of apremilast by the removal of the solvent.

In another general aspect, there is provided a stable amorphous form of apremilast wherein the stability is measured by an absence of conversion of the amorphous form of apremilast to a crystalline form of apremilast after the amorphous apremilast is exposed to a relative humidity of 5% at 40° C. or 60% at 25° C. for a period of at least three months.

In another general aspect, there is provided an amorphous solid dispersion of apremilast and a polymer, wherein the amorphous solid dispersion of apremilast is prepared by a process comprising grinding a solid-solid mixture of apremilast and a polymer under controlled humidity.

In another general aspect, there is provided a pharmaceutical composition comprising an amorphous form of apremilast and one or more pharmaceutically acceptable carriers, excipients or diluents.

In another general aspect, there is provided a pharmaceutical composition further comprising at least one polymer selected from hydroxypropyl methylcellulose acetate succinate, hydroxypropyl methyl cellulose, methacrylic acid copolymers, and polyvinyl pyrrolidone.

In another general aspect, there is provided a process for packing an amorphous form of apremilast, the process comprising
(a) placing an amorphous apremilast under nitrogen atmosphere in a non-permeable bag and tied;
(b) placing the bag of step (a) inside another bag, optionally containing oxygen busters and sealing it;
(c) optionally placing the bag of step (b) inside a triple laminated bag, optionally containing oxygen busters and sealing it; and
(d) the sealed triple laminated bag inside a high density polyethylene (HDPE) container and sealing it.

In another general aspect, there is provided an amorphous apremilast having particle size distributions wherein the $10^{th}$ volume percentile particle size (D10) is 50 µm or less, the 50th volume percentile particle size (D50) is 200 µm or less, or the 90th volume percentile particle size (D90) is 400 µm or less, or any combination thereof.

In another general aspect, there is provided an amorphous form of apremilast having a chiral purity of about 95% or more, or about 98% or more, or about 99% or more, or about 99.5% or more, or about 99.8% or more, or about 99.9% or more, as determined using high performance liquid chromatography (HPLC).

In another general aspect, there is provided an amorphous form of apremilast having a purity of about 95% or more, or about 98% or more, or about 99% or more, or about 99.5% or more, or about 99.8% or more, or about 99.9% or more, as determined using high performance liquid chromatography (HPLC).

BRIEF DESCRIPTION OF THE ACCOMPANYING DRAWINGS

FIG. 1 discloses the x-ray diffractogram (XRD) of the amorphous form of apremilast.

Figure 2:
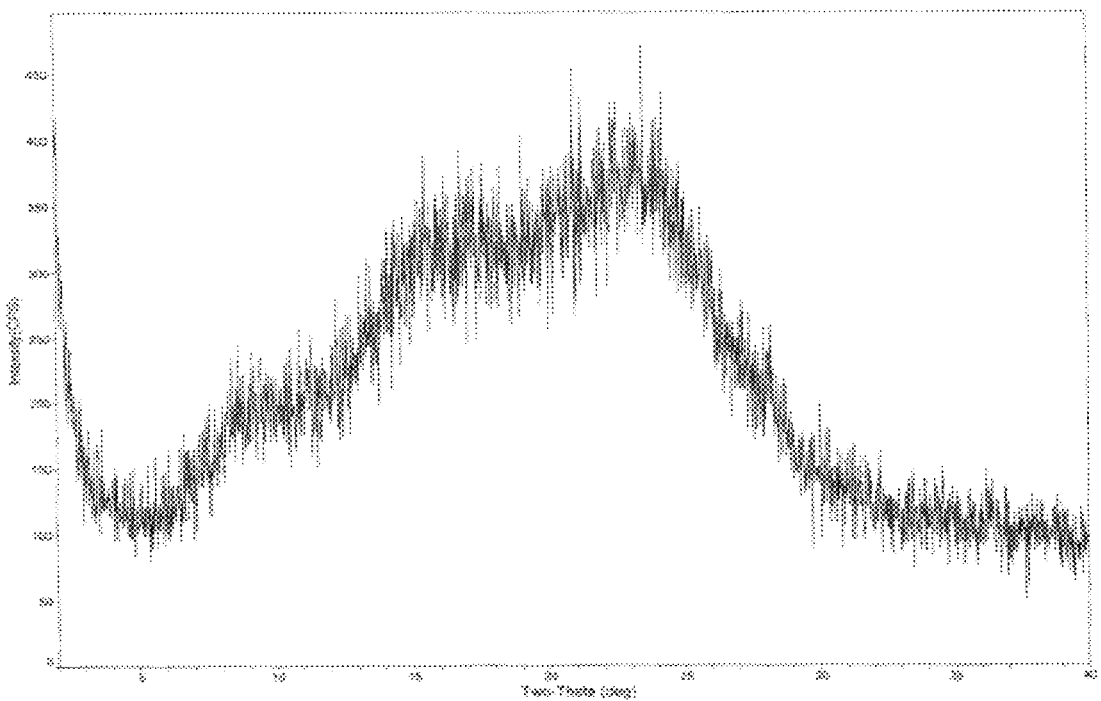

FIG. 2 discloses the x-ray diffractogram (XRD) of the amorphous form of apremilast as per example-4.

Figure 3:
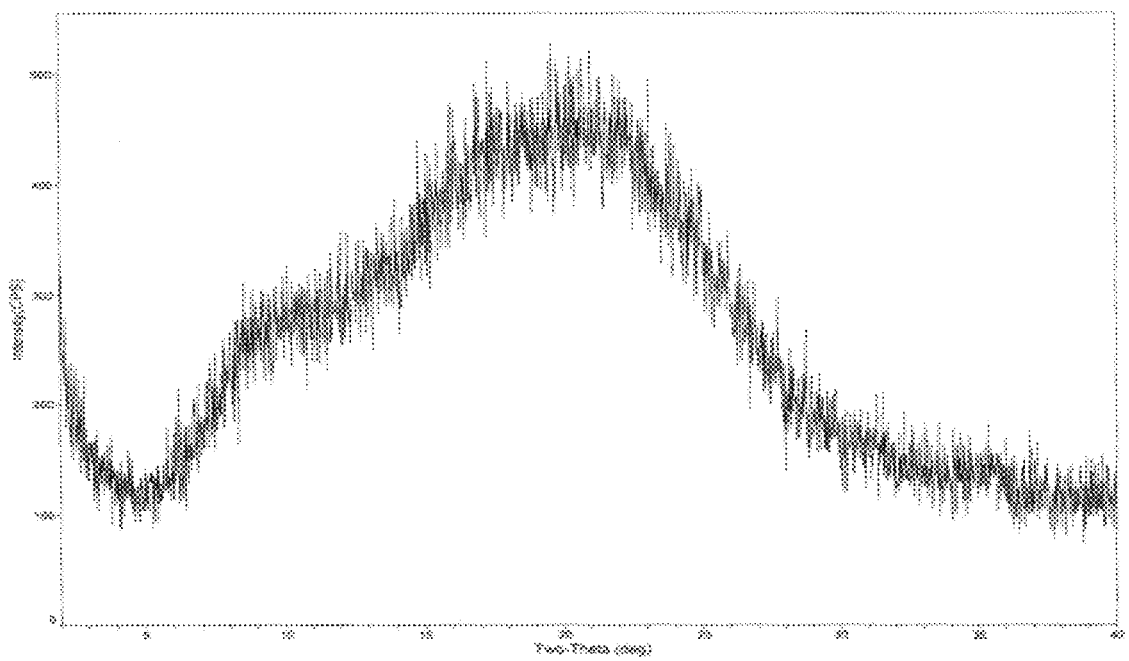

FIG. 3 discloses the x-ray diffractogram (XRD) of the amorphous form of apremilast as per example-5.

DETAILED DESCRIPTION OF THE INVENTION

The above and other objects of the present invention are achieved by the process of the present invention, which leads to amorphous apremilast suitable for pharmaceutical use and having greater stability. The invention provides a process for preparing amorphous form of apremilast.

Optionally, the solution, prior to any solids formation, can be filtered to remove any undissolved solids and/or solid impurities prior to the removal of the solvent. Any filtration system and techniques known in the art can be used.

All ranges recited herein include the endpoints, including those that recite a range "between" two values. Terms such as "about", "generally", "substantially," and the like are to be construed as modifying a term or value such that it is not an absolute. Such terms will be defined by the circumstances and the terms that they modify as those terms are understood by those skill in the art. This includes, at very least, the degree of expected experimental error, technique error and instrument error for a given technique used to measure a value.

As used herein, the term "controlled humidity" refers to a relative humidity in the range of 50±10%. In particular, the controlled humidity includes grinding process performed under controlled humidity followed by drying under controlled humidity for the preparation of an amorphous form of apremilast.

As used herein, the term "grinder" includes mixers, mills, blenders, and micronizers, or a combination thereof. The terms "grinding", "milling", "mixing", and "blending" and the like are interchangeable for achieving the homogeneous solid-solid mixture.

As used herein, the term "ball milling" as used herein means a process wherein shear forces are applied to a starting material by means of so-called milling balls located in a milling vessel. Typically and preferably, the milling vessel is rotated, wherein the milling balls collide with each other and with the API particles provided as the starting material. The ball mill preferred, may be planetary ball mill with model No. PM 100 and make of Retsch, Germany.

As used herein, the term "stable apremilast" includes an amorphous apremilast measured by an absence of conversion of the amorphous form of apremilast to a crystalline form of apremilast and free from residual solvents after the amorphous apremilast is exposed to a relative humidity of 75% at 40° C. or 60% at 25° C. for a period of at least three months.

As used herein, the term "solid dispersion" means any solid composition having at least two components. In certain embodiments, a solid dispersion as disclosed herein includes apremilast dispersed among at least one other component, for example a polymer.

As used herein the term "immobilize" with reference to the immobilization of the apremilast in the polymer matrix, means that molecules of the apremilast interact with molecules of the polymer in such a way that the molecules of the apremilast are held in the aforementioned matrix and prevented from crystal nucleation due to lack of mobility.

In one general aspect, there is provided an amorphous form of apremilast.

In another general aspect, there is provided an amorphous form of apremilast, wherein the amorphous apremilast is free from residual solvents.

In general, the term "free from residual solvents" herein means residual solvents are within the permissible ICH limits suitable for pharmaceutical preparations. For example but not limited to less than 0.5%, particularly less than 0.3% or more particularly less than 0.2%, or most particularly not in detectable amount.

In another general aspect, there is provided an amorphous form of apremilast, wherein the amorphous form is prepared by milling apremilast for sufficient time. In general, the step of milling apremilast comprises milling crystalline apremilast.

In general, the amorphous form of apremilast is stable and has not detectable quantity of the crystalline form of apremilast after the amorphous form of apremilast is exposed to a relative humidity of 75% at 40° C. or 60% at 25° C. for a period of at least three months.

In another general aspect, there is provided an amorphous solid dispersion of apremilast and a polymer.

In another general aspect, the amorphous solid dispersion of apremilast is prepared by a process comprising grinding a solid-solid mixture of apremilast and a polymer. In general, the step of grinding a solid-solid mixture of apremilast and a polymer comprises grinding a solid-solid mixture of crystalline apremilast and a polymer.

In general, the polymer may be a non-ionic polymer or an ionic polymer. The polymer comprises of hydroxypropylmethyl cellulose acetate succinate, hydroxypropylmethyl cellulose, methacrylic acid copolymers, and polyvinylpyrrolidone. In particular, polyvinylpyrrolidone of different grades comprises of K-15, K-30, K-60, K-90 and K-120 which may be used for the preparation of amorphous composition. More particular, hydroxypropylmethyl cellulose acetate succinate and polyvinylpyrrolidone K-30 may be used.

In general, the solid-solid mixture of apremilast and a polymer may be milled by grinding action between two surfaces. Such milling has been traditionally carried out in pharmacy practice by compounding using a pestle and mortar or a common mixer grinder. According to the invention, milling machines that work on substantially the same principle may be used in the present process. Examples of such milling machines include various makes of ball mills, roller mills, gyratory mills, multi-mills, Jet-mills, and the like.

In another aspect, a mill such as a Micros Super Fine Mill, Multi-Mill Sr. No. G.1.132, Retsch (Planetary ball mill), Jet-Mill from Midas Micronizer M-100 Aerosol (No. 154/07-08 or a common mixer grinder can be used. Alternatively another commercially available milling machine can be used.

The process parameter includes adding a solid-solid mixture of apremilast and hydroxypropylmethyl cellulose acetate succinate in a grinder. A specific grinder used can be small-scale to large-scale mixer grinder which can easily prepare the homogeneous mixture of two solids. For example purpose, Quadro dry mixing apparatus for providing lump-free homogenous blending to ensure proper mixing. The varieties of mills and mixers provided in Perry's Chemical Engineers' Handbook Seventh Edition by Robert H. Perry and Don W. Green can be used based on suitability are incorporated herein by reference in its entirety.

This grinding apparatus may consists of a water cooled jacketed bowl with the inside surface made of a suitable material such as Zirconium oxide, stainless steel, tungsten carbide, or aluminum oxide. Depending on the size of the grinder, the speed of rotation of the main shaft and the effective volume of the grinding chamber may vary. The effective volume of the grinding chamber may be in the range from about 0.45 liters to about 30 liters. For low capacity mills (such as 0, capacity 0.45 liters; or 5, capacity 4.8 liters), the speed of rotation of the main shaft is typically in the range from about 200 rpm to about 2000 rpm.

In general aspect, the grinder may be a typical milling apparatus. This milling apparatus may be typically charged with feed material such that from about 10% to 30% of the effective volume of the grinding chamber is occupied. Examples of methods of transferring materials well known in the art include manual transfer, gravity feed, pneumatic conveying (using a high velocity air stream), and vacuum transfer. Such methods, well known in the art, may be used with the process of this invention to charge the feed material into the grinding volume available between the bowl and the sub-shafts. For obtaining homogeneous solid-solid mixture, the apremilast and hydroxypropylmethyl cellulose acetate succinate may be mixed in a wide range of ratios.

The period of milling using the mill may vary depending on the size of the mill, the speed of rotation of the main shaft, the type of feed material, and the quantity of feed material. The effects of these variables are well known in the art and the invention may be worked over a range of these variables. Typically, the period of milling ranges from about 15 minutes to 300 minutes. In general, the apremilast is subjected to grinding involving attrition of the particles and machine surfaces.

In some aspects, the apremilast may be dispersed within a matrix formed by a polymer in its solid state such that it is immobilized in its amorphous form. The polymer may prevent intramolecular hydrogen bonding or weak dispersion forces between two or more drug molecules of apremilast. The solid dispersion provides for a large surface area, thus further allowing for improved dissolution and bioavailability of apremilast.

In some aspects, the ratio of the amount of weight of apremilast within the solid dispersion to the amount by weight of the polymer therein is from about 1:1 to about 1:10. The composition of apremilast with polymer, particularly hydroxypropylmethyl cellulose acetate succinate or polyvinylpyrrolidone may be prepared by using about 1:1 to about 1:10 polymers with respect to apremilast.

In another general aspect, there is provided a process for the preparation of an amorphous solid dispersion of apremilast and a polymer, the process comprising mixing apremilast with a polymer in one or more solvents and obtaining the amorphous solid dispersion of apremilast by the removal of the solvent.

The compound apremilast and a polymer (for example hydroxypropylmethyl cellulose acetate succinate or polyvinylpyrrolidone K-30) may be dissolved in one or more solvents selected from methanol, ethanol, isopropanol, acetone, ethyl acetate or mixture thereof with water. The amorphous solid dispersion may be obtained by the removal of the solvent. The removal of the solvent comprises one or more of evaporation by rotational distillation, evaporation under reduced pressure, spray drying, agitated thin film drying ("ATFD"), freeze drying (lyophilization), flash evaporation, and vacuum distillation thereby leaving the amorphous solid dispersion precipitated in a matrix formed by the polymer.

In another general aspect, there is provided a process for the preparation of an amorphous form of apremilast, the process comprising:
(a) providing a solution of apremilast in one or more of solvents; and
(b) obtaining an amorphous form of apremilast by the removal of the solvent.

Step a) involves providing a solution of apremilast in one or more solvents or mixture thereof.

The solution for step a) can be obtained by the known methods that include:
(i) direct use of a reaction mixture containing apremilast that is obtained in the course of its synthesis; or
(ii) dissolving apremilast in one or more solvents.

The solvents that may be used in step a) comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate, chlorinated hydrocarbons selected from methylene dichloride, ethylene dichloride, and chlorobenzene; acetonitrile; and polar aprotic solvents selected from dimethylformamide, dimethylacetamide, N-methylpyrrolidone, dimethyl sulfoxide, and mixtures thereof.

Step b) involves isolation of an amorphous form of apremilast from the solution of step a). The isolation may be affected by removing the solvent. The techniques which may be used for the removal of solvent comprises one or more of evaporation by rotational distillation, evaporation under reduced pressure, spray drying, agitated thin film drying ("ATFD"), freeze drying (lyophilization), flash evaporation, and vacuum distillation.

Alternatively, the isolation can be effected by addition of an anti-solvent to the solution obtain in step a), optionally by concentrating the solution obtained in the step.

The anti-solvents comprises one or more of hydrocarbons selected from hexanes, n-heptane, n-pentane, cyclohexane, and methylcyclohexane; aromatic hydrocarbons selected from toluene, xylene, and ethylbenzene; ethers selected diethyl ether, diisopropyl ether, t-butyl methyl ether, dibutyl ether, tetrahydrofuran, 1,4-dioxane, and 2-methoxy ethanol.

In another general aspect, there is provided a process of spray drying a solution of apremilast that involves the spray drying of a feed stock, which is prepared as discussed below, wherein any known form of apremilast may be used. The feed stock is dozed into the spray-drying instrument JISL Mini Spray-drier LSD-48 or Lab Ultima Spray-drier and spray drying is carried out under the following parameters.

| Sr. No. | Parameters | Conditions |
|---|---|---|
| a) | Feed pump | 10-50 rpm |
| b) | Inlet temperature | 35°-120° C. |
| c) | Outlet temperature | 30°-100° C. |
| d) | Aspirator rate | 1000-1500 rpm |
| e) | Vacuum for conveying the dry product | 30-120 mm of Hg |
| f) | Hot air supply | 2-4 Kg/cm$^2$ |
| g) | Atomizer Speed: | 40,000-100,000 rpm |

In the present invention, feed stock of apremilast is conveniently prepared by dissolving any known forms or wet cake of apremilast in one or more solvents comprises of acetone, $C_{1-4}$alcohols, $C_{2-6}$esters, acetonitrile, methylene dichloride, water or mixture thereof. In particular, methanol, ethanol, acetone, ethyl acetate, and methylene dichloride are used or such solvents that evaporate easily to afford dry product.

In another general aspect, there is also provided a process for the preparation of amorphous form of apremilast by spray drying a feed stock comprising apremilast and at least one polymer selected from hydroxypropylmethyl cellulose acetate succinate, hydroxypropylmethyl cellulose, methacrylic acid copolymers, and polyvinylpyrrolidone, which is also considered within the scope of invention.

In another general aspect, there is provided a process for the preparation of the amorphous form of apremilast, wherein the amorphous form of apremilast is prepared by grinding a solid-solid mixture of apremilast and hydroxypropyl methylcellulose acetate succinate. In general, grinding the solid-solid mixture is carried out under controlled humidity conditions.

In another general aspect, there is provided a process for the preparation of the amorphous form of apremilast, wherein the amorphous form of apremilast is prepared by grinding a solid-solid mixture of crystalline apremilast and hydroxypropyl methylcellulose acetate succinate.

In another general aspect, there is provided a stable amorphous form of apremilast which is at least stable during storage and drying.

In another general aspect, there is provided a stable amorphous form of apremilast wherein the stability is measured by an absence of conversion of the amorphous form of apremilast to a crystalline form of apremilast after the amorphous apremilast is exposed to a relative humidity of 75% at 40° C. or 60% at 25° C. for a period of at least three months.

In another general aspect, there is provided a process for packing an amorphous form of apremilast, the process comprising
(a) placing an amorphous apremilast under nitrogen atmosphere in a non-permeable bag and tied;
(b) placing the bag of step (a) inside another bag, optionally containing oxygen busters and sealing it;
(c) optionally placing the bag of step (b) inside a triple laminated bag, optionally containing oxygen busters and sealing it; and
(d) placing the sealed triple laminated bag inside a high density polyethylene (HDPE) container and sealing it.

In another general aspect, there is provided an amorphous apremilast having particle size distributions wherein the 10$^{th}$ volume percentile particle size (D10) is 50 μm or less, the 50th volume percentile particle size (D50) is 200 μm or less, or the 90th volume percentile particle size (1)90) is 400 μm or less, or any combination thereof. In particular, D90 is 100 μm or less and D50 is 50 μm or to less.

In another general aspect, there is provided an amorphous form of apremilast having a chiral purity of about 95% or more, or about 98% or more, or about 99% or more, or about 99.5% or more, or about 99.8% or more, or about 99.9% or more, as determined using high performance liquid chromatography (HPLC).

In another general aspect, there is provided an amorphous form of apremilast of having a purity of about 95% or more, or about 98% or more, or about 99% or more, or about 99.5% or more, or about 99.8% or more, or about 99.9% or more, as determined using high performance liquid chromatography (HPLC).

In further aspect, the apremilast may be micronized to achieve the better particle size distribution in order to make suitable Formulation.

The apremilast may be micronized prior to compression and shearing. Micronisation may be by any known method. Micronization is the process of reducing the average diameter of a solid material's particles, for example by milling or grinding. In one aspect an apremilast that has been subjected to a mechanical process which applies sufficient force to the apremilast that the process is capable of breaking coarse particles down to fine particles.

In another aspect micronization of the apremilast may be achieved using one or a combination of the following methods: ball milling, jet milling, jet blending, high-pressure homogenation, or any other milling method.

Ball milling is a milling method used in many of the prior art co-milling processes. Centrifugal and planetary ball milling may also be used.

Jet mills are capable of reducing solids to particle sizes in the low-micron to submicron range. The grinding energy is created by gas streams from horizontal grinding air nozzles. Particles in the fluidised bed created by the gas streams are accelerated towards the centre of the mill, colliding within. The gas streams and the particles carried in them create a violent turbulence and, as the particles collide with one another, they are pulverized.

Alternatively micronized apremilast may be produced by using a high energy media mill or an agitator bead mill, for example, the Netzsch high energy media mill, or the DYNO-mill (Willy A. Bachofen A G, Switzerland).

Powder X-ray Diffraction of amorphous apremilast can be obtained under following conditions.

X-ray powder diffraction spectrum was observed on a MF 2100 2KW X-ray Powder diffractometer of make Rigaku or PANalytical or equivalent having a Copper Kα-radiation at a voltage of 40 kV and 30 mA. Approximately 150 mg sample was gently flattened on a quartz plate without further processing (e.g. Grinding and sieving) and scanned from 2° to 40° at 0.010° sampling width.

According to another aspect, apremilast to be used herein as the starting material may be prepared by the known methods reported in the prior art i.e. by using the processes described in prior art for example, U.S. Pat. No. 6,020,358 and U.S. Pat. No. 6,962,940 which are incorporated herein as reference. The apremilast used as starting material can be of any known crystalline forms reported in the art.

The invention also encompasses pharmaceutical compositions comprising apremilast of the invention. As used herein, the term "pharmaceutical compositions" includes pharmaceutical formulations like tablets, pills, powders, liquids, suspensions, emulsions, granules, capsules, suppositories, or injection preparations.

Pharmaceutical compositions containing the apremilast of the invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

In another general aspect, there is provided a pharmaceutical composition comprising an amorphous form of apremilast and one or more pharmaceutically acceptable carriers, excipients and diluents.

In another general aspect, there is provided a pharmaceutical composition comprising an amorphous form of apremilast and one or more pharmaceutically acceptable carriers, excipients and diluents. In general, the pharmaceutical composition comprising an amorphous form of apremilast comprises at least one polymer selected from hydroxypropyl methylcellulose acetate succinate, hydroxypropyl methyl cellulose, methacrylic acid copolymers, and polyvinyl pyrrolidone.

In another general aspect, there is provided a pharmaceutical composition comprising an amorphous form of apremilast free from residual solvents and one or more pharmaceutically acceptable carriers, excipients or diluents.

In another general aspect, there is provided a pharmaceutical composition comprising a stable amorphous form of apremilast and at least one polymer having one or more pharmaceutically acceptable carriers, excipients or diluents.

The present invention is further illustrated by the following example which is provided merely to be exemplary of the invention and do not limit the scope of the invention. Certain modification and equivalents will be apparent to those skilled in the art and are intended to be included within the scope of the present invention.

EXAMPLES

Example 1

Preparation of Amorphous Apremilast

In 100 mL three necked round bottom flask equipped with mechanical stirrer, thermometer and an addition funnel, Apremilast (0.5 gm), polyvinyl pyrrolidone K-30 (4 gm) and 88% methanol in water (12.5 ml) were heated to 65-70° C. to obtain solution. The reaction mixture was stirred for 1 hour, concentrated under vacuum at 65-70° C. and degassed under vacuum for 1 hour at 70° C. to obtain the title compound in pure amorphous form.

Example 2

Preparation of Amorphous Apremilast

In 100 mL three necked round bottom flask equipped with mechanical stirrer, thermometer and an addition funnel, Apremilast (2 gm) and polyvinyl pyrrolidone K-30 (4 gm) were grinded in grinding bowl by using planetary ball milling (1 hour milling by 10 min interval every 15 min grinding at RPM 200). Further, the same material mixed in grinding bowl by using planetary ball milling (1 hour milling by 10 min interval every 15 min grinding at RPM 200) to obtain the title compound in pure amorphous form.

Example 3

Preparation of Amorphous Apremilast

In 100 mL three necked round bottom flask equipped with mechanical stirrer, thermometer and an addition funnel, Apremilast (2 gm) was grinded in grinding bowl by using planetary ball milling (1 hour milling by 10 min interval every 15 min grinding at RPM 200). Further, the same material mixed in grinding bowl by using planetary ball milling (1 hour milling by 10 min interval every 15 min grinding at RPM 200) to obtain the title compound in pure amorphous form.

Example-4

Preparation of Amorphous Apremilast

In 100 mL three necked round bottom flask equipped with mechanical stirrer, thermometer and an addition funnel, Apremilast (0.5 gm) and hydroxypropyl methylcellulose (0.5 gm) in 90% ethanol in water (15 mL, 30V) were heated at 65 to 70° C. to obtain solution. The content was stirred for 30 minutes at 25° C. to 30° C. To this, 1.0 g charcoal was added and stirred for 30 minutes at 80° C. The content was filtered through hyflosupercell, and the hyflosupercell pad is washed with 50 mL ethanol. The filtrate was spray dried in JISL Mini spray drier LSD-48 under the below conditions.

| Sr. No | Parameters | Conditions |
|---|---|---|
| a) | Feed pump | 10 rpm |
| b) | Inlet temperature | 100° C. |
| c) | Outlet temperature | 85° C. |
| d) | Hot air supply | 2 Kg/cm² |

The product was collected from cyclone and was further dried at 40° C.±5° C. under vacuum for 4 hours to obtain 4 gm of amorphous form of apremilast. The obtained product is free from residual solvents.

Example-5

Preparation of Amorphous Apremilast

In 250 mL three necked round bottom flask equipped with mechanical stirrer, thermometer and an addition funnel, Apremilast (9 gm) and methylene dichloride (90 mL) were stirred to prepare the feed stock. The content was filtered through hyflosupercell, and the hyflosupercell pad is washed with 50 mL methylene dichloride. The filtrate was spray dried in Lab Ultima spray drier under the below conditions.

| Sr. No | Parameters | Conditions |
|---|---|---|
| a) | Feed pump | 10 rpm |
| b) | Inlet temperature | 100° C. |
| c) | Outlet temperature | 85° C. |
| d) | Hot air supply | 2 Kg/cm² |

The product was collected from cyclone and was further dried at 40° C.±5° C. under vacuum for 4 hours to obtain 4 gm of amorphous form of apremilast. The obtained product is free from residual solvents.

Example 6

Preparation of Amorphous Apremilast

In 250 mL three necked round bottom flask equipped with mechanical stirrer, thermometer and an addition funnel, Apremilast (2.5 g) and hydroxypropyl methylcellulose (2.5 gm) were grinded in grinding bowl by using planetary ball milling (1 hour milling by 10 min interval every 15 min grinding at RPM 300). Further, the same material mixed in grinding bowl by using planetary ball milling (1 hour milling by 10 min interval every 15 min grinding at RPM 300) to obtain 3.75 g of pure amorphous form of apremilast. The obtained product is free from residual solvents.

While the present invention has been described in terms of its specific embodiments, certain modifications and equivalents will be apparent to those skilled in the art and are intended to be included within the scope of the present invention.

We claim:

1. An amorphous form of apremilast.
2. The amorphous form of apremilast according to claim 1, wherein the amorphous apremilast is free from residual solvents.
3. The amorphous form of apremilast according to claim 1, wherein the amorphous form is prepared by milling apremilast for sufficient time.
4. The amorphous form of apremilast according to claim 3, wherein the step of milling apremilast comprises milling crystalline apremilast.
5. The amorphous form of apremilast according to claim 1, wherein the amorphous apremilast is stable and has no detectable quantity of the crystalline form of apremilast after the amorphous form of apremilast is exposed to a relative humidity of 75% at 40° C. or 60% at 25° C. for a period of at least three months.
6. An amorphous solid dispersion of apremilast and a polymer, wherein the polymer is a non-ionic polymer or an ionic polymer comprising one or more of hydroxypropyl methylcellulose acetate succcinate, hydroxypropyl methylcellulose, methacrylic acid copolymers, and polyvinyl pyrrolidone.
7. The amorphous solid dispersion of apremilast according to claim 6, wherein the amorphous solid dispersion of apremilast is prepared by a process comprising grinding a solid-solid mixture of apremilast and the polymer.
8. The amorphous solid dispersion of apremilast according to claim 7, wherein the step of grinding a solid-solid mixture of apremilast and a polymer comprises grinding a solid-solid mixture of crystalline apremilast and the polymer.
9. A process for the preparation of an amorphous form of apremilast, the process comprising:
    (a) providing a solution of apremilast in one or more of solvents; and
    (b) obtaining the amorphous form of apremilast by the removal of the solvent.
10. The process according to claim 9, wherein the solvent comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate, chlorinated hydrocarbons selected from methylene dichloride, ethylene dichloride, and chlorobenzene; acetonitrile; and polar aprotic solvents selected from dimethylformamide, dimethylacetamide, N-methylpyrrolidone, dimethyl sulfoxide, and mixtures thereof.
11. The process according to claim 9, wherein the removal of the solvent comprises one or more of evaporation, evaporation by rotational distillation device, evaporation under reduced pressure, spray drying, agitated thin film drying ("ATFD"), freeze drying (lyophilization), flash evaporation, and vacuum distillation.
12. A process for the preparation of an amorphous form of apremilast, wherein the amorphous form of apremilast is prepared by grinding a solid-solid mixture of apremilast and hydroxypropyl methylcellulose acetate succcinate.
13. The process according to claim 12, wherein grinding the solid-solid mixture is carried out under controlled humidity conditions.
14. The process according to claim 12, wherein the step of grinding a solid-solid mixture of apremilast and hydroxypropyl methylcellulose acetate succcinate comprises grinding a solid-solid mixture of crystalline apremilast and hydroxypropyl methylcellulose acetate succcinate.
15. A pharmaceutical composition comprising an amorphous form of apremilast and one or more pharmaceutically acceptable carriers, excipients or diluents.
16. The pharmaceutical composition according to claim 15 further comprising at least one polymer selected from hydroxypropyl methylcellulose acetate succcinate, hydroxypropyl methylcellulose, methacrylic acid copolymers, and polyvinyl pyrrolidone.
17. A stable amorphous form of apremilast wherein the stability is measured by an absence of conversion of the amorphous form of apremilast to a crystalline form of apremilast after the amorphous apremilast is exposed to a relative humidity of 75% at 40° C. or 60% at 25° C. for a period of at least three months.

18. An amorphous solid dispersion of apremilast and a polymer, wherein the amorphous solid dispersion of apremilast is prepared by a process comprising grinding a solid-solid mixture of apremilast and a polymer selected from a non-ionic polymer or an ionic polymer comprising one or more of hydroxypropyl methylcellulose acetate succcinate, hydroxypropyl methylcellulose, methacrylic acid copolymers, and polyvinyl pyrrolidone under controlled humidity.

19. The dispersion according to claim 18, wherein the controlled humidity is a relative humidity in the range of 50±10%.

20. The dispersion according to claim 18, wherein the step of grinding a solid-solid mixture of apremilast and the polymer comprises grinding a solid-solid mixture of crystalline apremilast and hydroxypropyl methylcellulose acetate succinate.

* * * * *